United States Patent [19]
Weuster-Botz et al.

[11] Patent Number: 6,063,618
[45] Date of Patent: May 16, 2000

[54] DEVICE FOR THE SERIES CULTIVATION OF MICRO-ORGANISMS OR CELLS IN GASIFIED LIQUID COLUMNS

[75] Inventors: Dirk Weuster-Botz; Jutta Altenbach-Rehm, both of Aachen, Germany

[73] Assignee: Forschungszentrum Julich GmbH, Julich, Germany

[21] Appl. No.: 09/011,318

[22] PCT Filed: Aug. 3, 1996

[86] PCT No.: PCT/DE96/01485

§ 371 Date: Feb. 4, 1998

§ 102(e) Date: Feb. 4, 1998

[87] PCT Pub. No.: WO97/06239

PCT Pub. Date: Feb. 20, 1997

[30] Foreign Application Priority Data

Aug. 8, 1995 [DE] Germany .............................. 195 29 099

[51] Int. Cl.[7] ........................................................ C12M 3/00
[52] U.S. Cl. ........................................ 435/294.1; 435/296.1; 435/297.1; 435/304.1
[58] Field of Search ................................. 435/289.1, 294.1, 435/296.1, 297.1, 304.1; 261/122.1

[56] References Cited

FOREIGN PATENT DOCUMENTS

| 0 307 048 A2 | 3/1989 | European Pat. Off. . |
| 42 14 157 C1 | 8/1993 | Germany . |
| 2 268 187 | 1/1994 | United Kingdom . |

Primary Examiner—David A. Redding
Attorney, Agent, or Firm—Herbert Dubno

[57] ABSTRACT

A reaction apparatus has a plurality of reaction flasks whose bottoms can communicate with a sterile gas source and are provided with porous filter plates which permit the gas to flow into the vessel but prevent the liquid from passing out through the plates. The culture flasks are received in pockets on an upper plate of a double-bottom structure which can communicate through the upper plate between a space within the double bottom and the bottom of the culture flasks. The spiral gas feed is connected to the double-bottom space.

13 Claims, 4 Drawing Sheets 6,063,618

DEVICE FOR THE SERIES CULTIVATION OF MICRO-ORGANISMS OR CELLS IN GASIFIED LIQUID COLUMNS

CROSS REFERENCE TO RELATED APPLICATIONS

This application is a national stage of PCT/DE96/01485 filed Aug. 3, 1996 and based, in turn, on German national application 195 29 099.2 filed Aug. 8, 1995.

FIELD OF THE INVENTION

The invention relates to a device for the series cultivation of microorganisms or cells in gasified liquid columns and culture flasks suitable therefor.

BACKGROUND OF THE INVENTION

For carrying out series experiments on solid nutrient substrates, the use of agar plates is customary. In such cases, the microorganisms are applied as individual seeds to the solid culture layer and incubated to the respective reaction temperature. The material transport (substrate from the solid cultivation layer and oxygen from the gas phase) is effected purely diffusively.

The classical apparatus for the cultivation of microorganisms in series experiments is the shaker flask apparatus. Such apparatus allows reaction volumes from several milliliters to 1000 milliliters to be used to carry out many experiments in parallel with the aid of the shaker incubator. The energy input for dispersing the liquid phase (medium and microorganisms) is effected via a circular movement of all of the reaction vessels which are arranged on a platform. The oxygen input is effected only, in such cases, via a surface gasification. The material transport in the liquid phase is effected convectively. For miniaturization of this technique (so that still more experiments can be carried out in parallel) it has been proposed to use microtiter plates as reaction vessels. Use of this technique has been hindered by special problems in evaporation because of an unsatisfactory surface to volume ratio.

A technique which is extremely expensive from the apparatus point of view for carrying out series experiments with the microorganisms is the parallel use of laboratory fermenters. For this purpose apparatus must be provided which enables parallel processing of up to six fermentations with a single device. The energy input is here effected by standard stirring elements. Via a gasification device, volume gasification is possible.

OBJECT OF THE INVENTION

The object of the invention is to provide a relatively simple arrangement, from an apparatus viewpoint, for series culturing in which satisfactory gasification is ensured.

SUMMARY OF THE INVENTION

This object is achieved with a device according to the invention which comprises a series of culturing flasks with an open or perforated bottom which are provided above the bottom or the bottom opening with gas-permeable porous filter plates whose pore fineness and hydrophobicity suffices to prevent the escape of the liquid from a culture liquid column disposed thereabove, and which via the bottom provides a gas-type connection with a sterile gas feed line.

Such an arrangement of a series of cultivation flasks, which are connected via their bottoms with a gas distributor, can be equipped with different gas distributors in the form of feed pipe lines via bores on a series stand.

It is especially advantageous, however, to provide a gas-tight double bottom as the gas distributor and to equip it with a sterile inlet for gas as the sterile gas feed line, the double bottom having an upper plate with a series of gas outlet openings formed with respective receiving seats for sealing engagement with the cultivation flasks which rest on or are inserted in the seats. This means that between the upper bottom of the gas distributor and the lower end of the cultivation flasks, a sealing connection is provided coaxial with the gas connection bore of the gas distributor.

According to the invention, the following improvements especially result:

1. A substantial problem in the cultivation of aerobic microorganisms is the oxygen supply. By the use of gasified columns for the gasification of microorganisms for series experiments because of the volume gasification a significantly better oxygen supply to the microorganisms is possible than is obtainable with conventional shaker flasks. The difference in oxygen input characteristics between the surface gasification and volume gasification can be greater than one order of magnitude or power of 10 depending upon the surface/volume ratio.

2. The substantial problem with the use of data obtained in small reaction vessels is the translation of these results in the reactor. By the improvement in the oxygen supply with the gasified columns to values which are obtained in technological level reactors, the scaling up translation is significantly better especially since the process of oxygen supply which is used (volume gasification) is identical. The time for the development of processors to produce products with microorganisms is shortened.

3. By comparison with the use of parallel laboratory reactors for the cultivation of microorganisms for series experiments, the cost is substantially less in terms of apparatus operation with the use of gasified columns.

BRIEF DESCRIPTION OF THE DRAWING

The above and other objects, features, and advantages will become more readily apparent from the following description, reference being made to the accompanying drawing in which.

SPECIFIC DESCRIPTION

Figure 2:
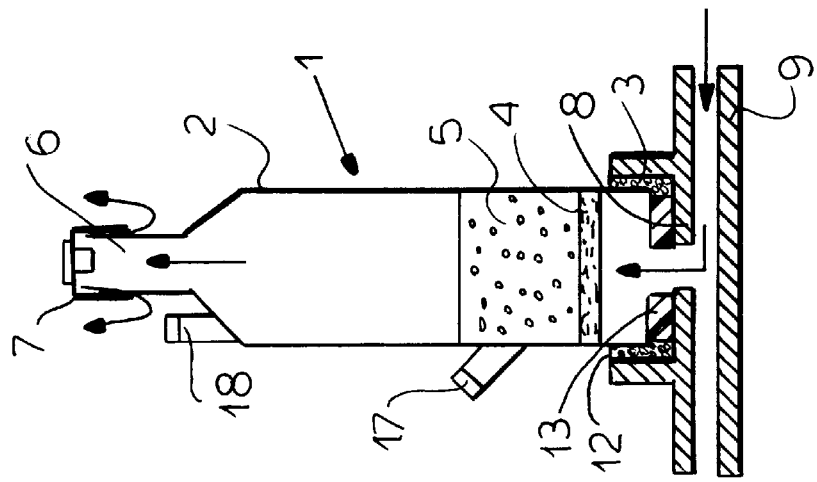
FIG. 2 is a cross section through an individual cultivation flask in detail.
Figure 1:
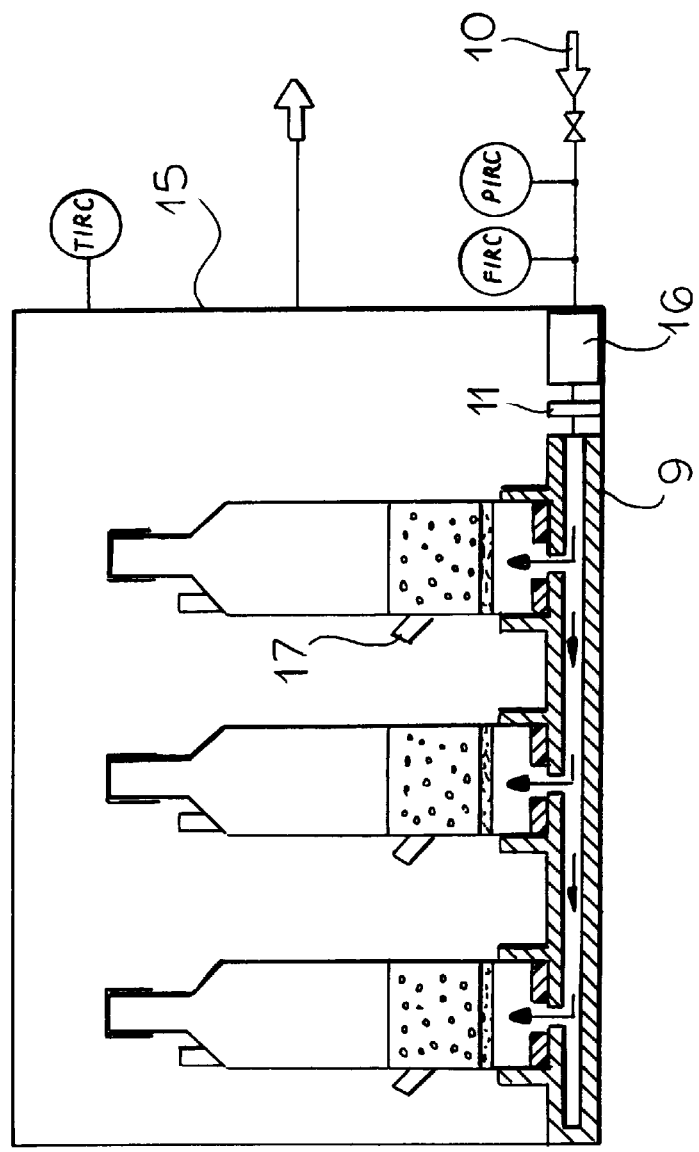
FIG. 1 is a vertical section through a series cultivation apparatus according to the invention.

FIG. 1 shows an arrangement of a plurality of culture flasks 1 which have been shown in greater detail in FIG. 2. A generally cylindrical glass vessel 2, which is open at the bottom or is provided with an opening for the inlet of gas, contains in its lower part a porous filter plate 4 (e.g. of borosilicate glass) especially across the total cross section, through which the glass is introduced into the liquid phase 5 (medium with microorganisms) lying thereabove. At the head of the flask 1 there is an opening 6 for receiving a standard device like, for example, a sterile stopper or aluminum cap 7, which enables discharge of the gas without contamination of the glass flask contents.

A multiplicity of culture flasks 1, preferably with an enclosed volume of 10 to 1000 ml and a diameter of 10 to 100 mm are (especially closed) uniformly distributed and fixed in pocket-like receiving seats 8 of a glass distributor 9 which is provided with corresponding connecting fittings for gas supply 10 to the individual culture flasks 1. This gas distributor 9 is autoclavable together with the culture flasks 1 fastened thereon.

Figure 3:
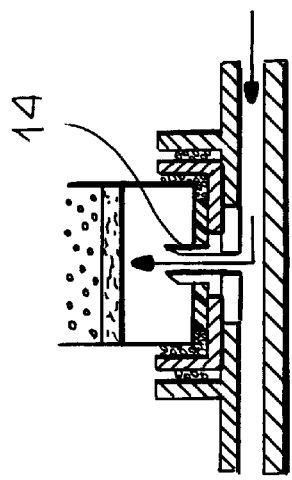
FIG. 3 is a cross section of a variant in the configuration of the receiving plate and the flask bottom.

The attachment of the culture flasks in or on the receiving seats 8 is effected advantageously via screw or bayonet connections (at 12) with sealing rings 13. Optionally piercing devices 14 are provided in the receiving seats of the gas distributor for accommodating the culture flasks 1 as has been shown in FIG. 3 and which pierce through a bottom membrane of the flask. Thus a separate sterilization and supplementary sterile connection of the gas distributor and culture flasks is possible.

For controlling the temperature the gas distributor with the individual culture flasks is installable in a temperature-controlled housing 15, for instance provided with a cover hood so that the reaction temperature can be controlled. The medium and the seeding of a biomass can be supplied by standard techniques after autoclaving to start the process. For this purpose a liquid volume 5 of a maximum of 50% of the enclosed volume of the culture flasks is especially desirable to prevent foaming over in the case of possible foam formation.

Even in the ungasified state, a penetration of medium into the gas distributor is suppressed since the culture flask is equipped with porous filter plates whose pore diameter is so fine that the hydrostatic pressure of the overlying liquid column is not sufficient to fill the capillaries of the porous filter plate. In general, filter plates with a pore diameter of at most 20 $\mu$m of a liquid column of about 10 cm in height in the ungasified state can be maintained above the porous filter plate. Additionally, the inner surface of the porous filter plates can be hydrophobilized by known means. Especially suitable techniques for producing hydrophobic glass surfaces are known from the silane and silicon chemistry.

Figure 4:
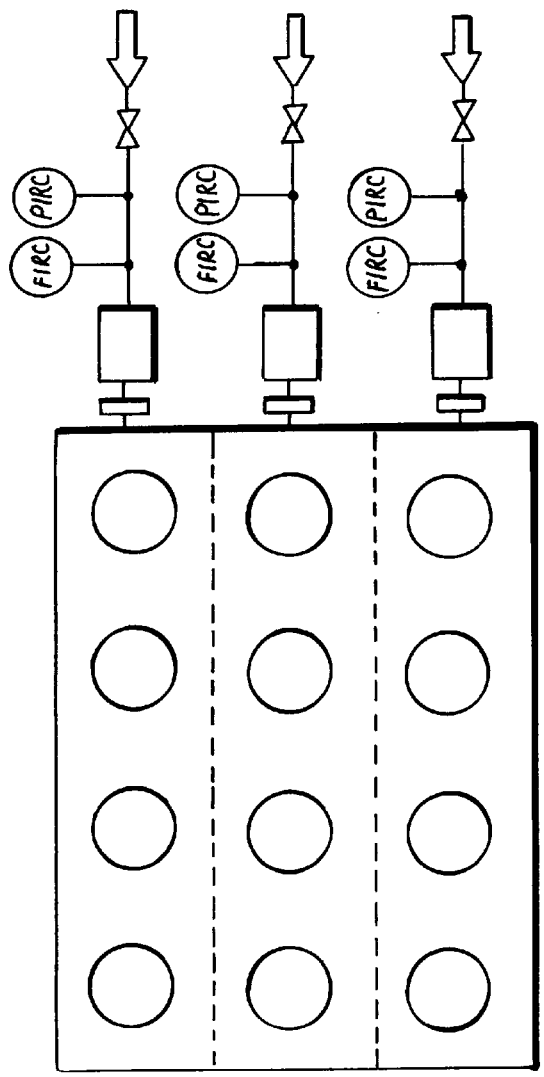
FIG. 4 is a layout of the arrangement for different gasification series, in plan view.

The gas for gasification is saturated with steam in the sterile filter 11 of the gas distributor 9 in a gas moistener (e.g. by means of corresponding washing flasks) so that a volume reduction in the gasified columns by evaporation is suppressed. The gas volume flow 9 (e.g. air or oxygen-enriched gas mixture) can be for example up to 2.5 l gas/(liter reaction volume per minute. By the use of a multiplicity of parallel gas-feed devices for each row of gasified columns, each different gas-feed device can be provided with another gas volume flow rate as has been indicated in FIG. 4.

For sampling during the reaction, the culture flasks can optionally be provided with lateral sampling fittings 17 having a septum through which, with the aid of cannula, a defined quantity of a sample can be sterilely withdrawn.

To accommodate measurement sensors (e.g. for measuring pH values or $pO_2$ values) optionally at the head of the gasified column, a further fitting 18 can be provided.

When aluminum caps ("Alucaps") 7 are used for the contamination-free removal of the gases from the gasified column, optionally a septum can be provided together with a connection to miniaturized substrate lines enabling continuous meeting of substrate or correction agents during the reaction.

The range of uses include:

The biotechnical research (as alternative to hitherto customary use of shaker flasks) and The development of industrial process for producing products with microorganisms, more than 90% of the experiments which are carried out in the framework of industrial process development are effected in shaker flasks.

The following examples illustrate the suitability of the apparatus of the invention:

EXAMPLE 1

Comparison of the volumetric oxygen incorporation coefficients ($k_L a$) of the culture flasks of the invention (gasified column), conventional shaker flasks and laboratory tube reactors.

Figure 6:
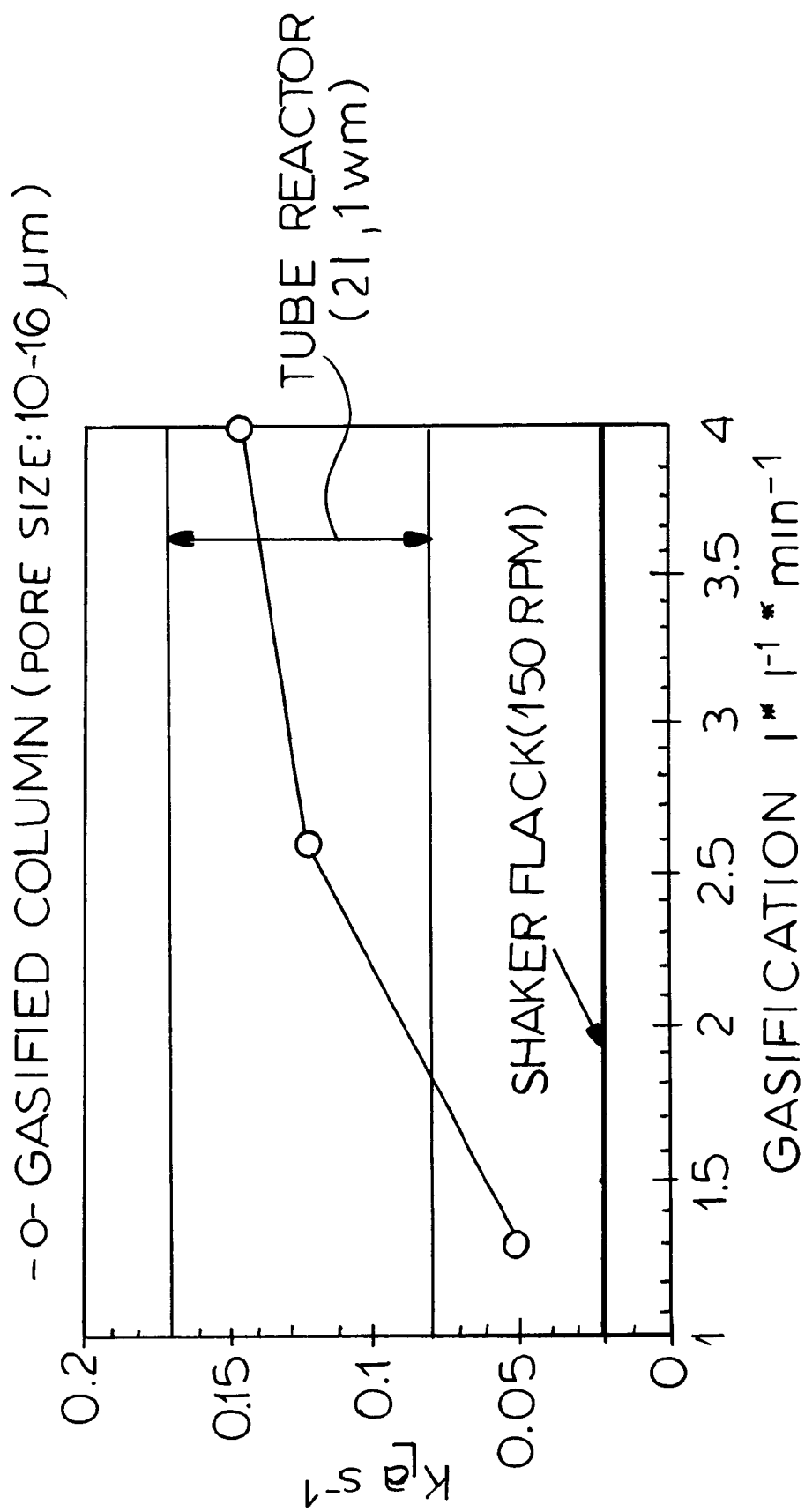
FIG. 6 is a graphic comparison of the volumetric material transfer coefficient ($k_L a$) for culture flasks according to the invention (gasified columns), shaker flasks and a 2 l tube reactor as determined by the sulphite method at 30° C.

The volumetric oxygen incorporation coefficients ($k_L a$) is determined according to the sulfite method in culture flasks (diameter 60 mm) with porous filter plates of borosilicate glass (pore size 10–16 $\mu$m with a working volume of 150 ml and different gas throughputs (T=30° C.). The obtained measurement results (see FIG. 6) show $k_L a$ values between 0.05 and 0.15 $s^{-1}$. For comparison, data is obtained under comparable conditions in shaker flasks and in a laboratory tube reactor (sulfite method, T=30° C.).

It is to be seen clearly that the volumetric oxygen incorporation coefficient of the culture flasks (gasified columns) lies clearly above the values attained in shaker flasks and achieve the order of magnitude of the laboratory tube reactor.

EXAMPLE 2

Comparison of the culturing of Coryne bacterium glutamicum in culture flasks according to the invention (gasified column) and in conventional shaker flasks.

For comparison of the fermentation process in culture flasks (gasified columns) and conventional laboratory shaker flasks, parallel formulations are made. As the exemplary system, the L-isoleucin production with a Coryne bacterium glutamicum strain (KK47x15) of the Institute for Biotechnology of the Research Institute Jülich is selected.

The porous filter plates for the culture flasks used in Example 1 (gasified columns) were hydrophobized before use in the fermentation as follows:

For pretreatment of the glass surface, the gasified column is boiled in 5% nitric acid for 4 hours with refluxing. After a 12 hour cleaning with distilled water, it is dried at 150° C.

For covalent bonding of methyl groups on the glass surfaces of the porous filter plates, the gasified columns are boiled with 5% trimethylchlorosilane in chloroform for 4 hours with refluxing. They are then washed three times with chloroform and dried for 48 hours at 50° C. in a water jet vacuum. That was followed by 12 hours of cleaning with distilled water and subsequent drying.

Production of the preculture: 80 ml of sterilized complex medium is sterilely mixed with 20 ml of sterile glucose solution (100 g/l) in a 1000 ml shaker flask and incubated with 2% inoculum of the strain for 12 hours at 30° C. and 155 rpm.

After heat sterilization of the 1000 ml shaker flask and the culture flask (gasified column, pore diameter of the porous filter plates: 10–16 μm), 90 ml of sterilized medium and 10 ml of inoculum from the preculture are sterilely introduced into the culture flask of the shaker flask (glucose 20 g/l). The shaker flasks were cultured in the shaker incubator 30° C. and 155 rpm. The culture flasks (gasified columns) were incubated in the incubator at 30° C. and aerated with 0.6 l/min of humidified air.

Figure 5:
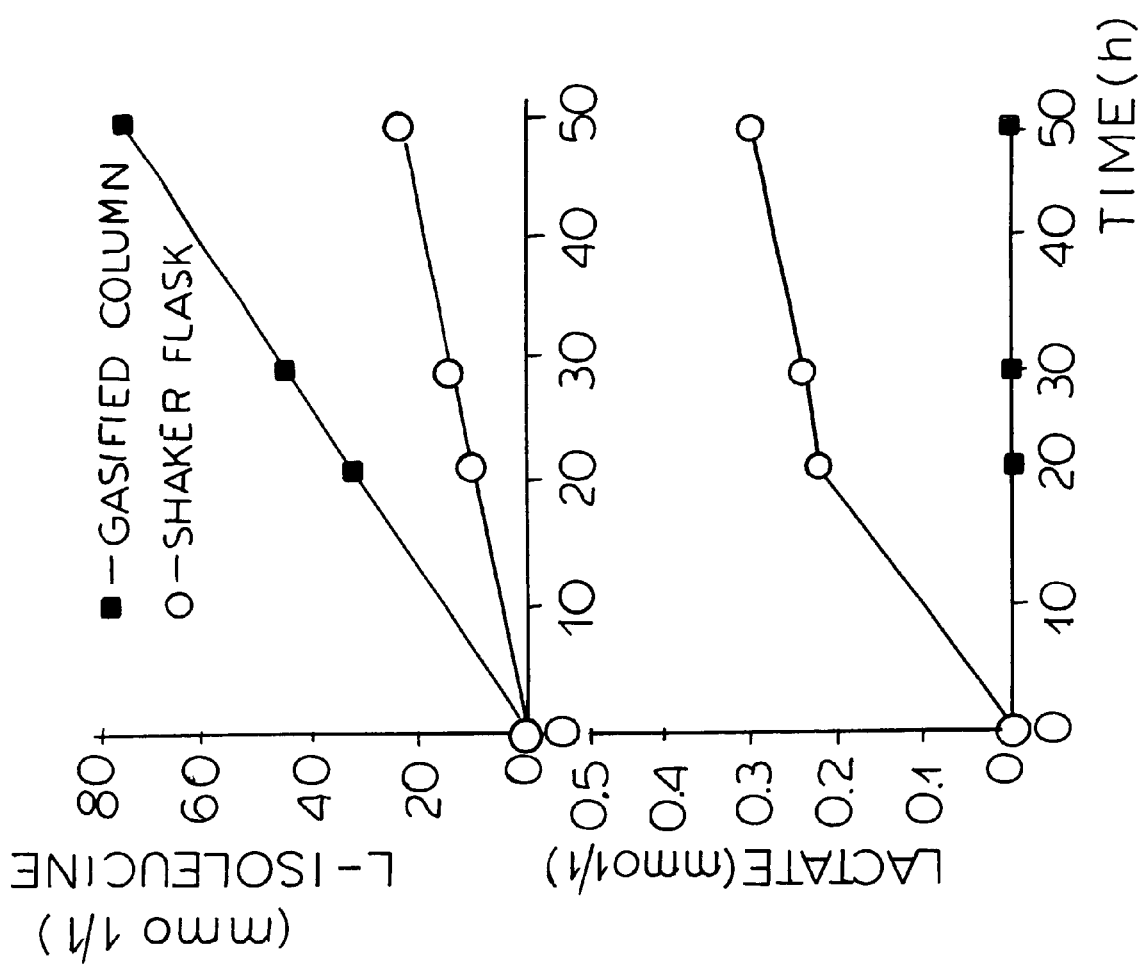
FIG. 5 is a graphic comparison of the parallel cultivation of Coryne bacterium glutamicum bacteria for the production of L-isoleucin in cultivation flasks gasified columns according to the invention and in shaker flasks.

The results show that the culture flasks (gasified columns) because of the significantly greater oxygen incorporation, 4 times higher L-isoleutin concentrations were obtainable (see FIG. 5). From a lactate analysis it was found that in the gasified column there was no oxygen limiting (no lactate byproduct was detectable). While the shaker flasks were found to be oxygen limited (lactate detectable, see FIG. 5).

We claim:

1. An apparatus for the sterile cultivation of microorganisms or cells in gasified liquid columns, comprising a series of culture flasks with gas-penetrable bottoms which are equipped above the bottom with gas-permeable porous filter plates, whose pore fineness and hydrophobicity is sufficient to suppress liquid flow from the culture liquid column found thereabove and which via their bottoms are connected hermetically with a sterile gas feed line.

2. An apparatus according to claim 1, further comprising a gas-tight double bottom with a sterile inlet for a gas forming a gas distributor and connected with a sterile gas feed line, the double bottom having an upper plate provided with a series of receiving seats for the hermetic reception of the culture flasks and provided with gas outlet openings communicating with said bottom of said flasks.

3. An apparatus according to claim 1 wherein said culture flasks each have an upper closure cap having a septum insert.

4. An apparatus according to claim 1 wherein each of said culture flasks has an upper septum connection suitable for the introduction of a measurement sensor.

5. An apparatus according to claim 1 wherein at least one of said culture flasks has a lateral fitting with a septum connection for sampling.

6. An apparatus according to claim 1, further comprising receiving seats which are formed pocket-like with passages communicating with a space in said double bottom and with connecting elements cooperating with the lower peripheries of the culture flasks and which are suitable with a sufficient pressing pressure to form a ring seal between the lower flask ends and the gas distributor.

7. An apparatus according to claim 6 wherein said connection elements are screw or bayonet connections.

8. An apparatus according to claim 6, further comprising piercing needles in the receiving seat bottom and perforatable membrane at said bottoms of said culture flasks pierceable by said needle.

9. An apparatus according to claim 1, further comprising a cover hood with thermomstating engaging over the series of flasks.

10. An apparatus according to claim 2 wherein respective partition walls subdivide the double bottom into one or more compartments.

11. An apparatus according to claim 1, further comprising gas supply lines which are each provided with a sterile filter and gas moisturizer.

12. An apparatus according to claim 11, further comprising pressure and flow meters in the sterile gas feed line.

13. An apparatus according to claim 11, further comprising devices which hold the gas moisturizer at the same temperature as a culture space in said flasks.

* * * * *